US00PP35570P2

(12) United States Plant Patent
Sattler

(10) Patent No.: US PP35,570 P2
(45) Date of Patent: Jan. 9, 2024

(54) HOP PLANT NAMED 'YQH-1320 EXP'

(50) Latin Name: *Humulus lupulus*
Varietal Denomination: YQH-1320 EXP

(71) Applicant: Tim Sattler, Yakima, WA (US)

(72) Inventor: Tim Sattler, Yakima, WA (US)

( * ) Notice: Subject to any disclaimer, the term of this patent is extended or adjusted under 35 U.S.C. 154(b) by 0 days.

(21) Appl. No.: 17/803,751

(22) Filed: Nov. 8, 2022

(51) Int. Cl.
*A01H 5/02* (2018.01)
*A01H 6/28* (2018.01)

(52) U.S. Cl.
USPC ..... Plt./236
CPC ..... *A01H 6/28* (2018.05)

(58) Field of Classification Search
USPC ..... Plt./236
CPC ..... A01H 6/28; A01H 5/02
See application file for complete search history.

(56) References Cited

PUBLICATIONS

Mill95hops, Mill95hops.com/blog, Dec. 5, 2022, 8 pages (Year: 2022).*
BSG, bsgcraft.com, 1 page (Year: 2023).*

* cited by examiner

*Primary Examiner* — Keith O. Robinson
(74) *Attorney, Agent, or Firm* — Michelle Bos Legal LLC

(57) ABSTRACT

'YQH-1320 EXP' is a new hop plant notable for its abundant cones, tolerance to heat, and tolerance to powdery mildew.

7 Drawing Sheets

Latin name: *Humulus lupulus.*
Variety denomination: 'YQH-1320 EXP'.

BACKGROUND OF THE VARIETY

'YQH-1320 EXP' is a new and distinct hop plant of unknown parentage discovered by the inventor as a chance seedling in a cultivated hop field near St. Mary's, Id. in 2015. The 'YQH-1320 EXP' plant was first asexually reproduced by cuttings near Toppenish, Wash. and has been observed to remain true to type over successive asexually propagated generations.

BRIEF DESCRIPTION OF THE VARIETY

'YQH-1320 EXP' hop plant was first selected for its abundant cones, tolerance to heat, and tolerance to powdery mildew. Comparisons of 'YQH-1320 EXP' to similar varieties 'Cascade' (not patented) and 'Bitter Gold' (not patented) appear in Table 1 below.

TABLE 1

Comparison of 'YQH-1320 EXP' to Similar Varieties

| | 'YQH-1320 EXP' | 'Cascade' | 'Bitter Gold' |
|---|---|---|---|
| Aroma | Pineapple, mango, passionfruit, orange zest | Blackberry, floral, spice | Stone fruit, tropical fruit |
| Alpha Acids | 7.5% to 9.5% | 6% to 8% | 12% to 14% |
| Yield (lbs/acre) | 2400 lb | 2000 lb | 2000 lb |

BRIEF DESCRIPTION OF THE PHOTOGRAPHS

Photographs were taken at Wapato, Wash. in August 2022. The photos depict current season growth of hop bines, leaves and cones produced from root crowns planted in 2021.

DETAILED BOTANICAL DESCRIPTION OF THE VARIETY

Figure 1:
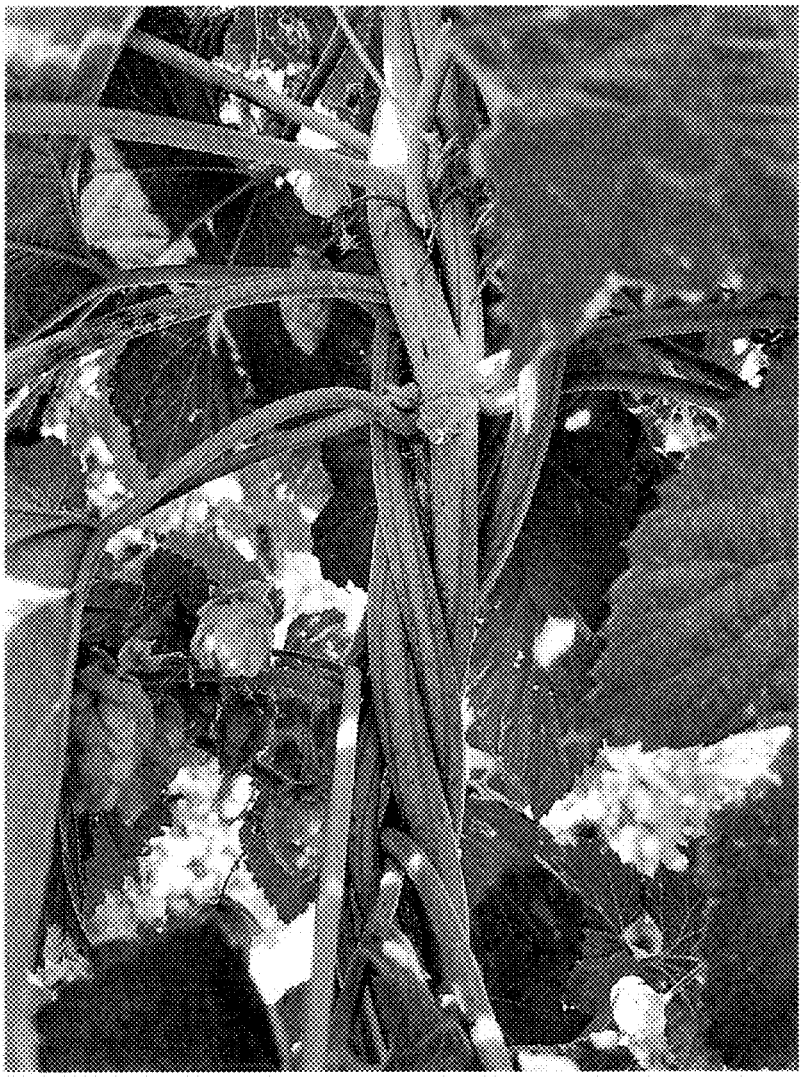
FIG. 1 shows the bine of the 'YQH-1320 EXP' hop plant.
Figure 2:
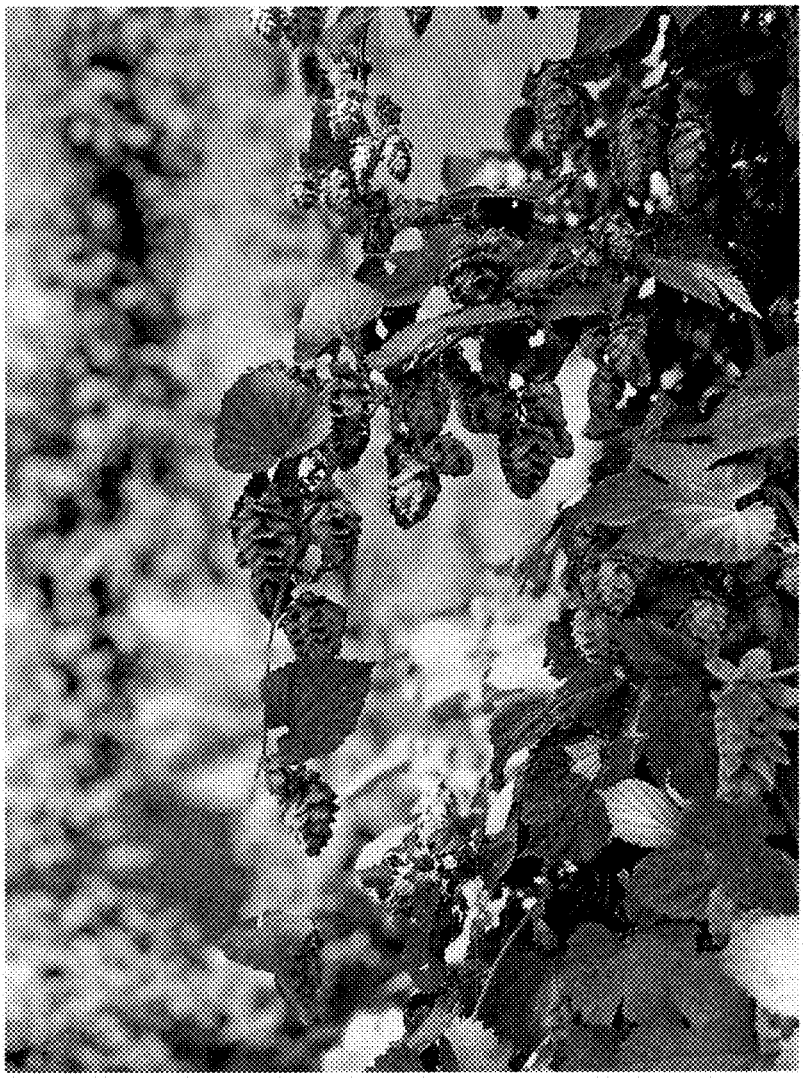
FIG. 2 shows cones and leaves on a 'YQH-1320 EXP' hop plant.
Figure 3:
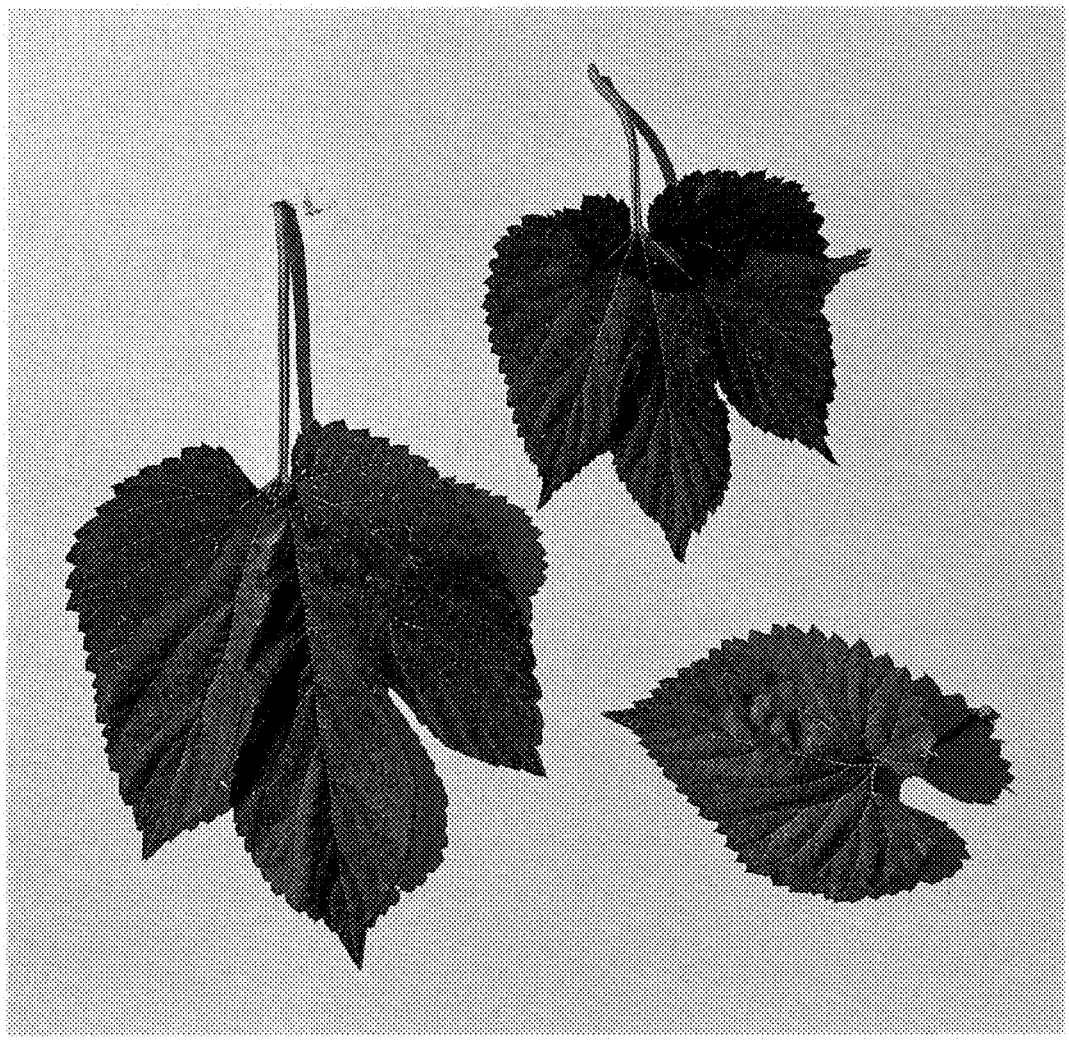
FIG. 3 shows the upper surface of a mature leaf of the 'YQH-1320 EXP' hop plant.
Figure 4:
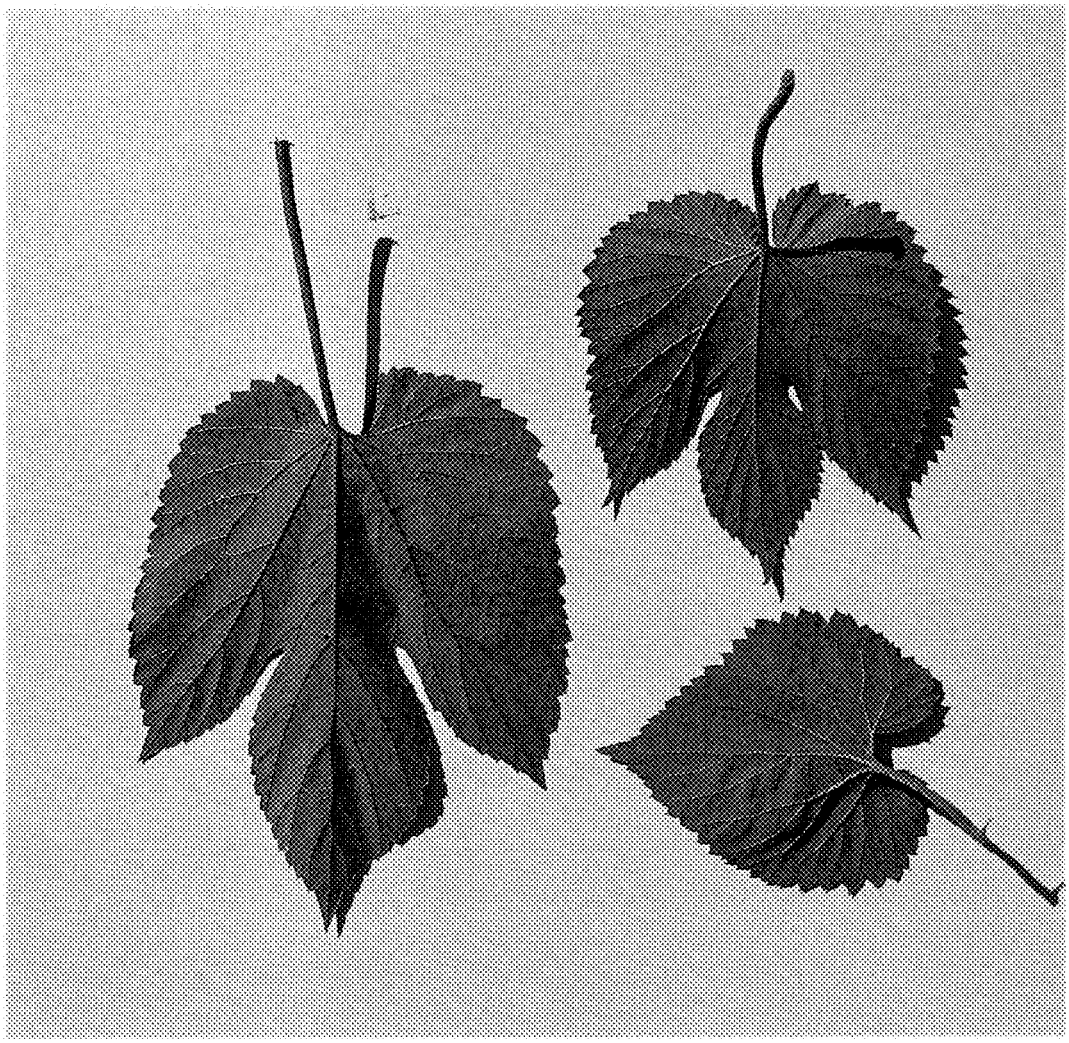
FIG. 4 shows the lower surface of a mature leaf of the 'YQH-1320 EXP' hop plant.
Figure 5:
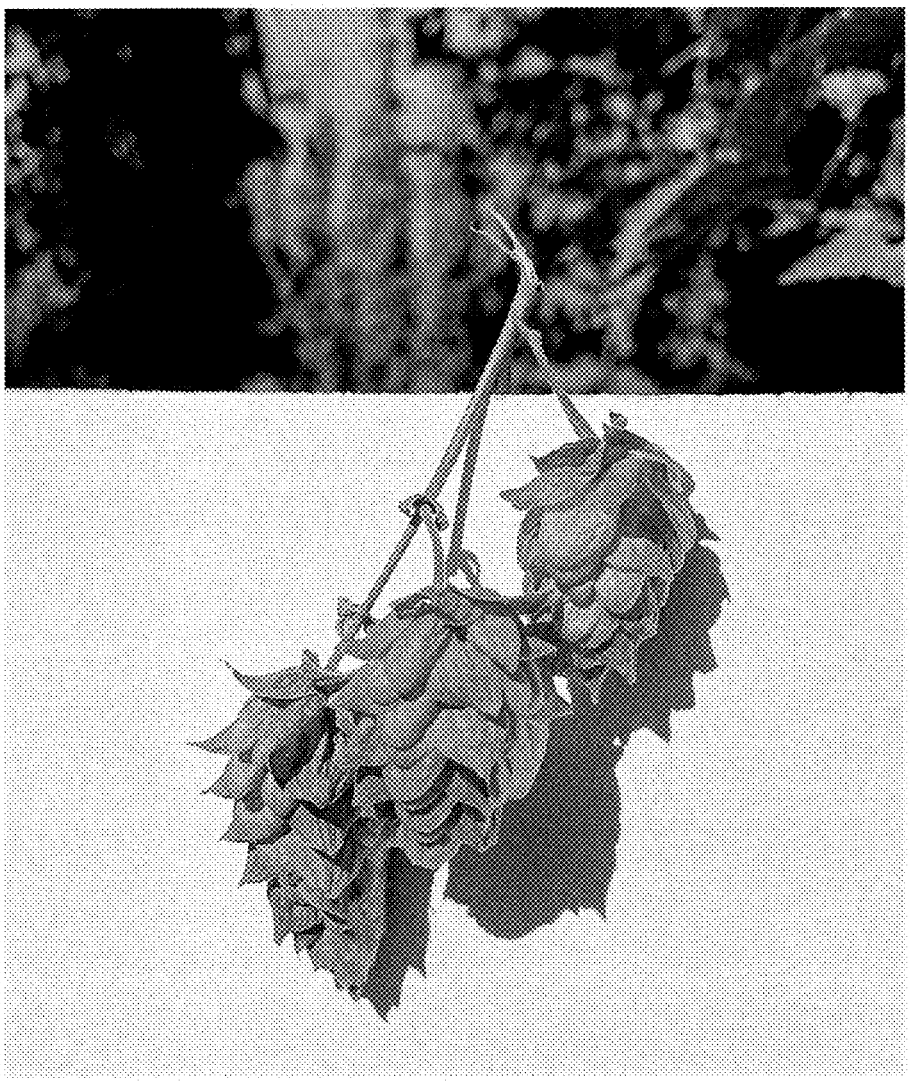
FIG. 5 shows a whole cone of the 'YQH-1320 EXP' hop plant.
Figure 6:
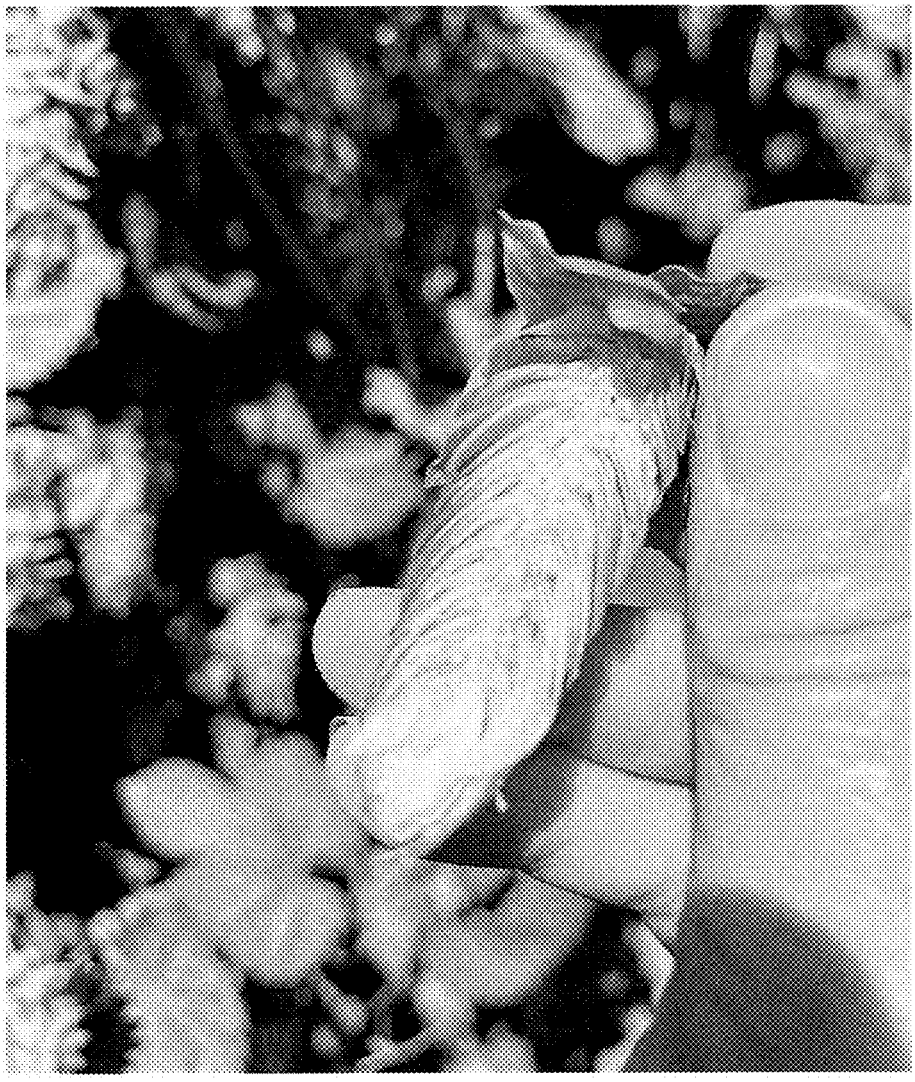
FIG. 6 shows a sectioned cone of the 'YQH-1320 EXP' hop plant.
Figure 7:
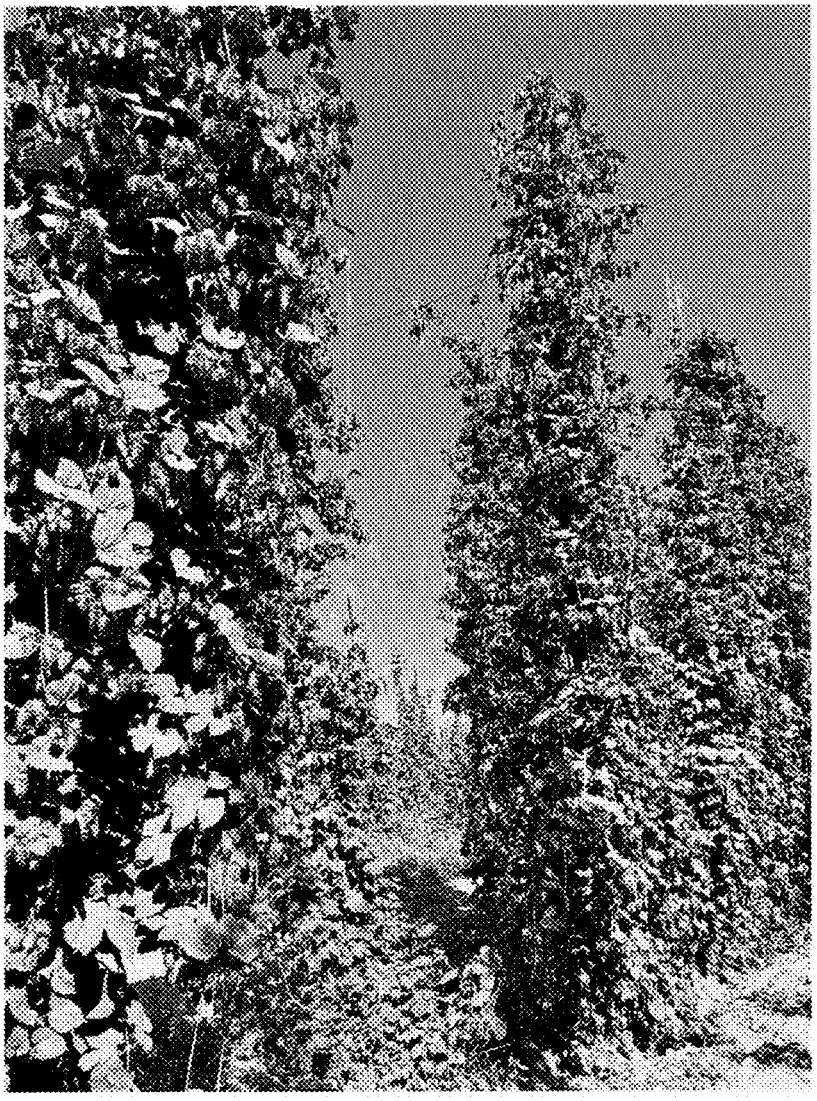
FIG. 7 shows a 'YQH-1320 EXP' hop plant approximately 2 weeks before harvest.

The following-detailed botanical description is based on observations made during the 2022 growing season at Wapato, Wash. Description is of current-season growth from hop crowns planted in 2021. All colors are described according to The RHS Colour Chart (Royal Horticultural Society, London, $6^{th}$ ed. 2015). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Bine:

*Color.*—Yellow-green 145A.
*Stripe.*—Narrow, distinct.
*Stripe color.*—Yellow-green 144A.
*Anthocyanin coloration.*—Absent.
*Stipule color.*—Yellow-green 145A.

*Stipule direction.*—Downward.
*Diameter.*—8 mm to 12 mm, average 10 mm.
*Average internode distance.*—25 cm to 30 cm on mature bine.
*Form.*—Climbing vine with drooping laterals.

Leaves:
*Leaf arrangement.*—Opposite.
*Leaf shape.*—Cordate and palmate.
*Average length* (*cordate mature leaf*).—7 cm to 12 cm.
*Average width* (*cordate mature leaf*).—6.5 cm to 12 cm.
*Average length* (*palmate mature leaf*).—12 cm to 15 cm.
*Average width* (*palmate mature leaf*).—12 cm to 15 cm.
*Color-upper surface, mature.*—Green NN137A.
*Color-lower surface, mature.*—Yellow-green 146A; vein yellow-green N148A.
*Color-upper surface, immature.*—Green NN137A.
*Color-lower surface, immature.*—Yellow-green 146A.
*Number of leaf lobes.*—Usually 3 on palmate leaves.
*Margin.*—Serrate.
*Average serrations per inch.*—5 to 7.
*Leaf apex.*—Acuminate.
*Pose.*—Upward facing.
*Texture-upper surface.*—Glabrous; blistering absent.
*Texture-lower surface.*—Smooth, veins prominent.
*Petiole length.*—2.5 cm to 7 cm; average 5 cm.
*Petiole diameter.*—2 mm to 3 mm.
*Petiole color.*—Yellow-green 146C.

Laterals:
*Length* (*at about* 40 *cm from ground*).—Varies, mostly 90 cm to 120 cm.
*Diameter.*—4 mm.
*Color.*—Yellow-green 144A.
*Internode length.*—17 cm to 25 cm; average about 20 cm.
*Stipule position.*—Outward to downward.
*Stipule color.*—Yellow-green 144A.

Cones:
*Time of flowering.*—Early, about 1 week before 'Cascade'.
*Length.*—30 mm to 60 mm; average 45 mm.
*Diameter.*—Average 20 mm.
*Number of cones per basal lateral node.*—15 to 40, usually about 25 to 30.
*Cone shape.*—Elongated with pointed tip.
*Cone compactness.*—Open bracts, somewhat compact.
*Average cone weight.*—900 mg.
*Bract color.*—Alternating darker and lighter bracts; darker bracts yellow-green 144A tip fading to yellow-green 144D at base; lighter bracts yellow-green 144C at tip fading to yellow-green 144D at base.
*Bract shape.*—Ovate.
*Bract tip shape.*—Acute to acuminate.
*Bract tip position.*—Lighter bracts curved inward, darker bracts held out.
*Bract length.*—13 mm to 15 mm.
*Bract width.*—10 mm to 12 mm.
*Bracteole shape.*—Cordate.
*Bracteole tip shape.*—Acuminate.
*Bracteole length.*—10 mm.
*Bracteole width/diameter.*—10 mm.
*Bracteole color.*—Yellow-green 144A.
*Strig size, compactness.*—2 mm diameter, compact.
*Lupulin gland quantity.*—Moderate.
*Lupulin gland shape.*—Rounded, slightly flat.
*Lupulin color.*—Yellow 9A.
*Yield per acre.*—2400.
*Harvest maturity.*—Mid-season (Sep. 1, 2022).
*Shattering potential at harvest.*—Low.
*Heat tolerance.*—Tolerant.
*Disease resistance/susceptibility.*—Good tolerance to powdery mildew (*Podosphaera macularis*).
*Aroma.*—Pineapple, mango, passionfruit, orange zest.

Analytical data:
*Alpha acids* (*spectrophotometric method*).—7.5% to 9.5%.
*Beta acids.*—5.7%.
*Total oil.*—2.1 ml/100 g.
*Myrcene* (*as % of total oils*).—54%.
*Caryophyllene* (*as % of total oils*).—5.2%.
*Humulene* (*as % of total oils*).—9.7%.

The invention claimed is:

1. A new and distinct hop plant (*Humulus lupulus*) named 'YQH-1320 EXP' substantially as described and illustrated herein.

* * * * *